(12) United States Patent
Pinnell et al.

(10) Patent No.: US 6,743,449 B2
(45) Date of Patent: Jun. 1, 2004

(54) TOPICAL COMPOSITION COMPRISING OLIVE LEAF EXTRACT

(75) Inventors: Sheldon R. Pinnell, Durham, NC (US); Mostafa M. Omar, Franklin Lakes, NJ (US)

(73) Assignee: Skinceuticals, Inc., Garland, TX (US)

( * ) Notice: Subject to any disclaimer, the term of this patent is extended or adjusted under 35 U.S.C. 154(b) by 0 days.

(21) Appl. No.: 10/074,974

(22) Filed: Feb. 13, 2002

(65) Prior Publication Data

US 2003/0152656 A1 Aug. 14, 2003

(51) Int. Cl.$^7$ ............... A61K 35/78; A61K 7/42
(52) U.S. Cl. ............ 424/725; 424/774; 424/59
(58) Field of Search ............ 424/59, 774, 195.1, 424/725, 94.1, 69; 514/789, 54; 554/212

(56) References Cited

U.S. PATENT DOCUMENTS

| | | | | |
|---|---|---|---|---|
| 4,704,280 A | * | 11/1987 | Bates | 424/195.1 |
| 5,378,461 A | * | 1/1995 | Neigut | 424/94.1 |
| 5,466,455 A | | 11/1995 | Huffstutler, Jr. | |
| 5,496,553 A | | 3/1996 | Wilson et al. | |
| 5,998,641 A | * | 12/1999 | Ganguli et al. | 554/212 |
| 6,358,542 B2 | | 3/2002 | Cuomo et al. | |

FOREIGN PATENT DOCUMENTS

AU 200159311 A * 11/2001

OTHER PUBLICATIONS

Hanbury, On the febrifuge properties of the olive (Olēa europaea L.), unknown publication information.
Shasha, On the oleuropein, the bitter principle of olives, vol. 26:1948–1954, 1960.
Redman, In vivo antiviral chemotherapy. . ., Antimicrobial Agents & Chemotherapy 1966, 497–502.
Fleming, Isolation of a bacterial inhibitor from green olives, Appl. Micro. 18:856–860, 1969.
Petkov, Pharmacological analysis of the iridoid oleuropein, anrneim.–Forsch (Drug Res.) 22:1476–86 1972.
Fleming, Antimicrobial properties of oleuropein and products of its hydrolysis from green olives, Appl. Micro. 26:777–782, 1973.
Benavente–Garcia, Antioxidant activity of phenolics extracted from Olea europaea L. leaves, Food Chem. 68:457–462, 2000.

* cited by examiner

Primary Examiner—Patricia Patten
(74) Attorney, Agent, or Firm—Lynn E. Barber

(57) ABSTRACT

A non-aqueous method of extracting olive leaves, and products formed containing the olive-leaf extract. The resulting extract is used, preferably together with vitamins C, E and A or components thereof to form a skin treatment product that has efficacy as a photoprotectant and antioxidant.

9 Claims, 2 Drawing Sheets

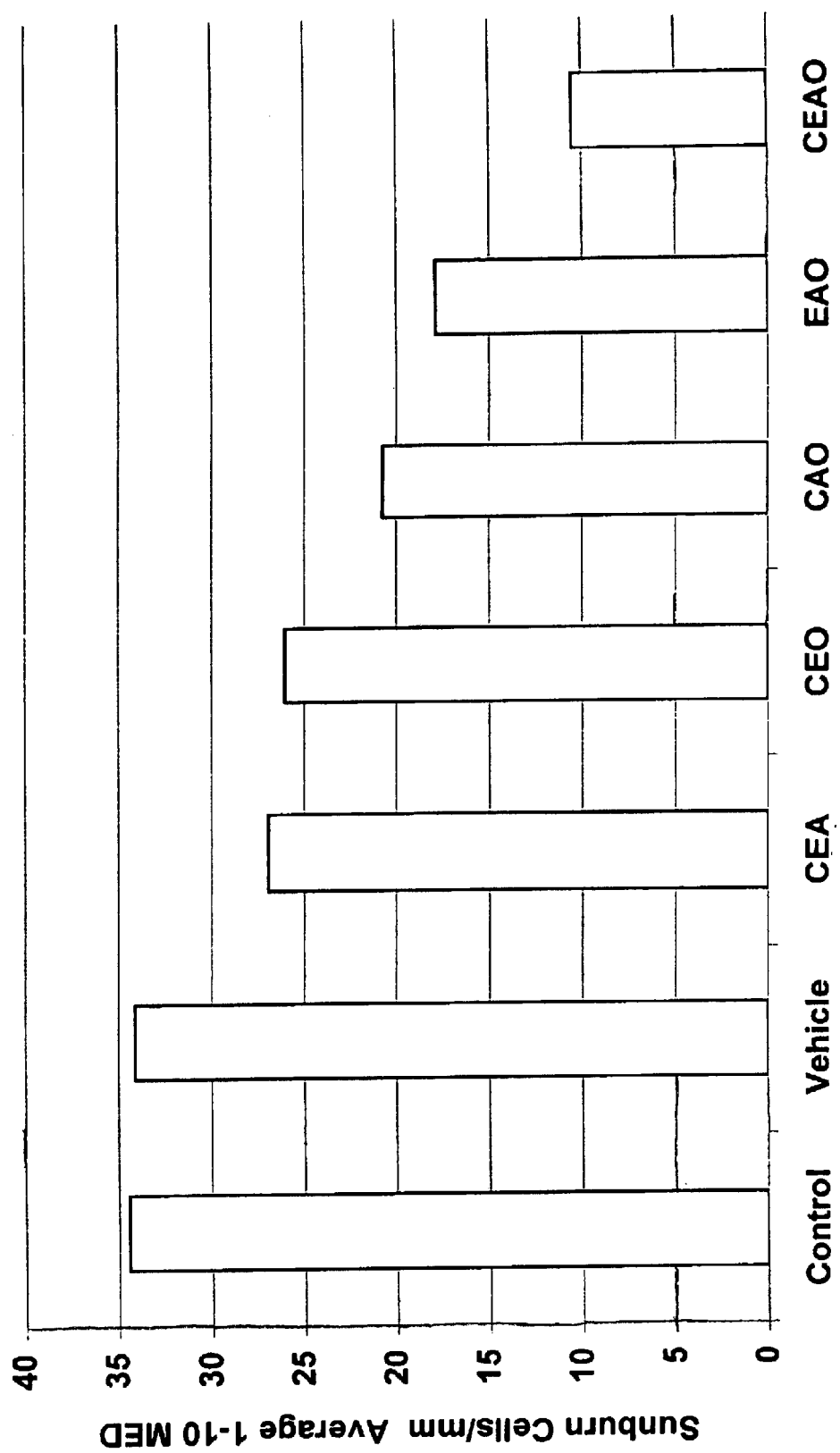

TOPICAL COMPOSITION COMPRISING OLIVE LEAF EXTRACT

BACKGROUND OF THE INVENTION

1. Field of the Invention

This invention relates to products that reduce damage that is caused to skin by the sun, and in particular, to products containing olive-leaf extract together with vitamin components.

2. Description of the Related Art

Ultraviolet radiation causes oxidative damage to the skin, including immunosuppression, which can cause skin cancer, alter the behavior of skin cancer, typically by making the cancer more aggressive, or cause photoaging. Much of this damage is preventable if clothing covers the skin, or where this is not practical, by topical products. UVA (340–400 nm) is linked to accelerated skin aging, causing DNA strand breakage and oxidation of nucleic acids, and UVB (290–320 nm) is a carcinogen. Standard sunscreens, however, while providing protection against UVB, do not fully protect against long-wave UV light (UVA) that is present at higher levels in sunlight and is not filtered by glass. Because of the growing incidence of skin cancer, there is an increased need for topical products that are more protective than standard sunscreens.

Both systemic antioxidants (e.g., oral vitamin C and vitamin E) and topical antioxidants (topical vitamin E and vitamin C) have been proposed as photoprotectants. A stable topical ascorbic acid solution has been developed (U.S. Pat. No. 5,140,043; Pinnell et al., Dermatol. Surg. 27:137–142, 2001) that is capable of traversing the stratum corneum of the skin, and thus resists being washed off of the skin, and provides both photoprotective and anti-inflammatory effects. Related commercial products exist that provide a) 20% L-ascorbic acid, or b) 15% L-ascorbic acid, 2% zinc sulfate and 1% α-tocopherol (vitamin E) (SkinCeuticals, Inc., Dallas, Tex.). Concentrations of about 5–25% L-ascorbic acid resulted in maximum levels of L-ascorbic acid in the skin, where a reservoir of L-ascorbic acid remained even without daily application to the skin.

One problem with antioxidant solutions is that they are inherently unstable (chemical instability and color instability), since antioxidants work by giving up an electron to neutralize oxidative damage and stop the reactive process. Thus, heat, light, air, metal contamination, and other generators of reactive oxygen can destroy antioxidants in solution.

While vitamin E has been shown to be useful in skin-treatment, its stability is also difficult to ensure. Stable aqueous solutions of lipophilic α-tocopherol at concentrations as high as 5% have been developed using bioflavonoid antioxidants and emulsifiers such as Tween 20, 60, 80 and Brij 30 and 72 at concentrations from 1–50%. This has allowed formulations of previous solutions of 15% L-ascorbic acid, 2% zinc sulfate and 1% α-tocopherol.

Extracts of various plant parts have been used for many different types of products, including products for the treatment of skin. The reduced incidence of certain cancers in the Mediterranean region has been attributed in part to the high consumption of olive oil in the Mediterranean diet. Virgin olive oil, obtained from the olive fruits, has long been known to have anti-inflammatory effects.

Historically, olive leaf has been used as a remedy for treating fevers and malaria. Several reports have shown that olive plant has the capacity to lower the blood pressure in animals and increase the blood flow in coronary arteries, relieve arrhythmia, and prevent intestinal muscle spasms.

Certain biophenolic molecules, such as oleuropein and hydroxytyrosol, known as the "bitter principle" in olive oil, inhibit pro-oxidative processes, which is the primary reason for the stability of virgin olive oil, and these compounds also increased the ability of human low density lipoprotein (LDL) to resist oxidation and reduced the plasma levels of total, free and ester cholesterol. Similarly, the specific phenolic compounds in olive oil and other olive plant parts have been found to have a marked antiedematous effect and to inhibit the enzyme myeloperoxidase, with oleuropein having the greatest inhibitory activity. Oleuropein has been shown to have cytotoxic effects on tumor cell lines, and to inhibit or delay the rate of growth of a range of bacteria and microfungi, including pathogens such as Salmonella, Staphylococcus, and *Haemophilus influenzae*.

Solid phase extraction methods have been used to separate phenolic components from olive fruit, as has a solid-liquid extraction procedure with diatomaceous earth and various eluents. In the extraction of the active ingredients from olive plants, there are several problems related to separation of the active fraction from the inactive fraction, as well as to purification of the active fraction.

Leaves of the olive (*Oleo europaea*), as well as the leaves of a number of other plants, are also known to contain high levels of secoiridoid glucosides such as oleuropein. Previous olive-leaf extracts have generally been obtained using aqueous chromatographic procedures, resulting in a lower oleuropein content, due to residual degradative enzymes present in the aqueous extracts. A typical concentration of oleuropein in such extracts is about 3%–18%.

It is therefore an object of the invention to provide a method for extraction of olive leaves that is nonaqueous and yields a high level of oleuropein. It is a further object of the invention to provide compositions containing this olive-leaf extract that are useful for skin treatment.

Other objects and advantages will be more fully apparent from the following disclosure and appended claims.

SUMMARY OF THE INVENTION

The invention herein is a non-aqueous method of extracting olive leaves. The resulting extract is used, preferably together with vitamins C, E and A to form a skin-treatment product that has efficacy as a photoprotectant and antioxidant. The invention also includes methods for treatment of skin with the product containing olive-leaf extract.

Other objects and features of the inventions will be more fully apparent from the following disclosure and appended claims.

BRIEF DESCRIPTION OF THE DRAWINGS

FIG. 2 is a table showing the sunburn cells per mm at 1–10× MED after use of the formulations shown in FIG. 1.

DETAILED DESCRIPTION OF THE INVENTION AND PREFERRED EMBODIMENTS THEREOF

Figure 1:
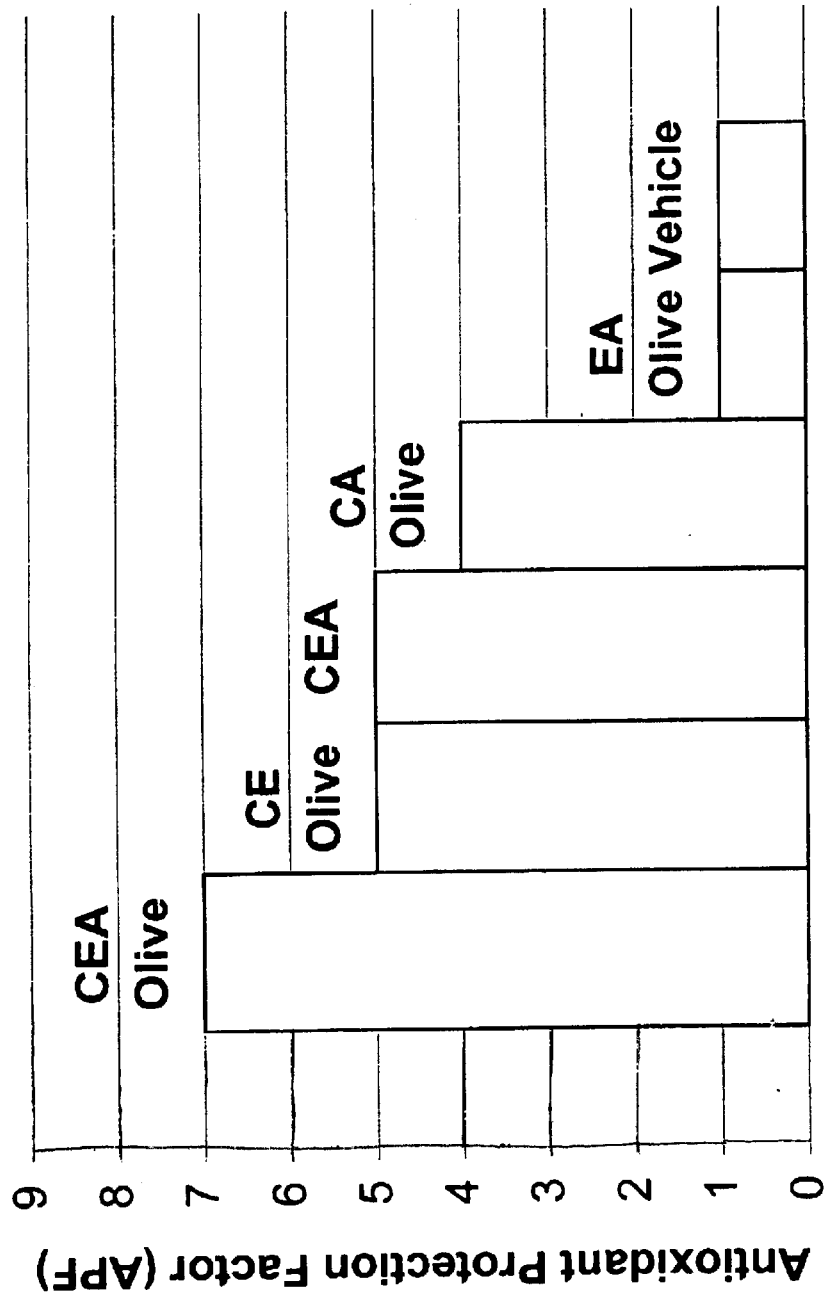
FIG. 1 is a table showing the antioxidant protection factor of various formulations having one or more of the following components: C-vitamin C; E-vitamin E; A-vitamin A; O or olive-olive extract; and the vehicle, as described in Example 1.

The present invention provides a method of obtaining an olive-leaf extract, and formulations containing said extract.

The photoprotection effect provided by the antioxidant formulations of the invention offer advantages over sunscreens per se, since they provide a reservoir of protection within the skin that cannot be removed.

In general, the procedure for the isolation of the active ingredients according to the method of the invention in based on selective solvent extraction and avoiding exposure to any levels of heat that would degrade the extract. The extraction method can vary with the scale and purpose of the extraction process, as well as with the nature of the raw material, and preferably utilizes chromatography to provide more rapid and accurate results.

The four main steps of the invention comprise:
a) preparing the raw materials, including drying the raw materials;
b) liberation of the secoiridod base by treating the dried materials with one or more suitable solvents to obtain the desired purity;
c) extraction of the active fraction with an organic solvent or a mixture of organic solvents, and removal of the organic extract by filtration; and
d) purification of the active fraction from the organic extract.

The raw plant materials need to be reduced to a moderately coarse powder by suitable means before the extraction, to facilitate effective contact of the solvent with the secoiridoid-containing tissues and cells. Since the active ingredients in olive plants are accompanied by certain enzymes capable of affecting hydrolysis of the active fraction, these enzymes must be inactivated before or during extraction of the active fraction. This is particularly important when fresh plant materials are used.

The olive enzymes may be inactivated by using at least one of the following steps, selected depending on the material being used, which are general steps used in the extraction of natural products:
a) drying the raw materials, for example, at 100° C. for 1–2 hours until the moisture content becomes below 1%, followed by slow drying at a low temperature as long as the moisture content is higher than 2%. This is required for raw materials that like to hold water even in dry state. This step can take more than 24 hours in a low temperature oven (50–60° C.);
b) placing the dried plant material into boiling water or boiling alcohol for 30 minutes to inactivate the enzymes. Use of boiling alcohol is preferred over use of boiling water; because the boiling alcohol treatment is carried out at lower temperature and also alcohol denatures the enzymes even at cold temperatures. The alcohol can also be removed faster from the plant materials than can water, and therefore the boiling water treatment needs to be followed by another period of oven drying;
c) boiling either fresh or dry raw materials in acetone. This treatment is not preferred because of the acetone's odor and the fact that acetone may not be safe to use in manufacturing processes;
d) pre-treating the plant material with acid at pH 1–2 at cold temperature (preferably below 20° C., because the internal enzymes, such as β-glucosidase start to be active from 37–41° C., which pH and temperature are maintained until the extraction is done) prior to extraction to kill the enzymes and aid in liberating the glycosides from its sugar content; this allows extraction of the glycosides in the form of aglycone after freeing the molecules from the sugar portion;
e) carrying out the initial extract at low temperature (10–15° C.) in the presence of magnesium sulfate; or
f) freeze-drying (lyophilization).

The extraction process, including inactivation of the enzymes to form the extract of the invention, preferably includes the following steps:
a) forming an initial extract of the plant material, comprising a treatment step selected from the group consisting of: (i) grinding olive leaves to a fine powder after they have been dried (preferably in a vacuum to eliminate the water content) in the presence of an anti-enzymatic compound; (ii) inactivating plant enzymes by boiling the plant material; and (iii) treating the plant material with acid at cold temperature;
b) continuously extracting the initial extract with a non-aqueous organic solvent, filtering and concentrating to form a first paste;
c) removing the non-aqueous solvent;
d) suspending the first paste in water, boiling, filtering, and re-concentrating to form a second paste; and
e) combining the second paste with alcohol and activated food-grade charcoal, boiling, filtering and re-concentrating to form the final extract.

The final extract preferably contains about 6–10% oleuropein.

Preferably the anti-enzymatic compound is $MgSO_4$ at a concentration of 0.1–1%, and most preferably at 0.25%. The non-aqueous solvent in step b) is preferably selected from the group consisting of petroleum ether, benzene, hexane, chloroform, and mixtures thereof. Most preferably the solvent is chloroform. The continuous extraction is preferably performed at 70° C. for 48 to 72 hours and includes maceration of the ground olive leaves. The solvent is removed by distillation in step c). In the preferred formulation, one part of the second paste is combined with two parts alcohol and one part activated food-grade charcoal. Each boiling step is performed for about two hours.

To check the level of the active ingredients (enzymes) in the extract, after each step of the extraction, the extract is dissolved in dimethylsulfoxide (DMSO) at 5 mg/ml and filtered. The extraction procedure for each extraction step is carried out by adding enough organic solvent (generally one part dried plant materials to 4–5 parts solvent), and macerating the raw materials for 48–72 hours before filtering the extract and concentrating under vacuum, with sufficient extraction steps being done so that the final extract paste has 70–75% solids. The first portion of the extract contains more active ingredient than the second, which contains more than the third. During each extraction, a sample is taken from the extract and tested for the presence of the active ingredient. After a fourth extraction of the raw materials, in most cases, there is no remaining active ingredient in the extract. Then the extraction procedure is terminated.

The filtrate is injected into HPLC equipment (Hewlett Packard, series HP1100), with a stationary phase C18 Lichrospher 100 analytical column (250×4 mm). The flow rate is 1 ml/min and the absorbance changes are monitored at 280 nm. The mobile phase for the chromatographic analysis are: A. acetic acid: water (5:95%); B. acetonitrile, a linear gradient from 95% A and 5% B. The phenolic compounds in olive extracts are identified by their retention times and compared with their corresponding standards by UV spectra. The main components of the extract of the invention are oleuropein, hydroxytyrosol, verbacoside, triterpenoid B-sitosterol and 3 flavonoidal glycosides, the first two of which are the important ingredients in the extract, with the other components not affecting the performance of the extract.

The product of the invention is preferably formulated to contain olive extract according to the invention, plus vitamins C, E and A, or components thereof. Formulations of 15% L-ascorbic acid (vitamin C), or 15% L-ascorbic acid plus 1% α-tocopherol (found in vitamin E) were found not to degrade after 6 months in glass containers. Concentrations of about 5–25% L-ascorbic acid resulted in maximum levels of L-ascorbic acid in the skin, where a reservoir of L-ascorbic acid remained even without daily application to the skin.

Vitamin E consists of 8 molecules including four different tocopherols and four different tocotrienols. While the preferred embodiment utilizes alpha-tocopherol, the predominant form of vitamin E in the body, one or more of the components, or other sources of one or more of the components of vitamin E, may be utilized instead, as more information becomes known about the particular characteristics of the components. Addition of α-tocopherol to solutions containing L-ascorbic acid enhances color stability of solutions containing L-ascorbic acid. A concentration of about 1–2% α-tocopherol is preferred, since higher concentrations typically result in oily formulations, and because maximal skin absorption seems to occur at about 1%.

In the preferred product composition of the invention, there is at least about ½% of an olive extract, preferably utilizing the extracted olive leaves as described above; 5–25% L-ascorbic acid (vitamin C); ½–2% vitamin E component(s); and ½–2% vitamin A. Most preferably the formulation comprises 1% of the final olive-leaf extract of claim 1; 15–20% L-ascorbic acid; 1–2% vitamin E component; and 1% vitamin A. The olive extract comprises at least one antioxidant phenolic compound, preferably selected from the group consisting of oleuropein and hydroxytyrosol. The vitamin E component is selected from the group consisting of tocopherols and tocotrienols and may comprise α-tocopherol. The product may also contain 1–5% zinc sulfate. The final pH of the product is preferably about 3.0 to 3.5 but may be in the range of 2.0 to 4.5.

The product composition in its preferred embodiment also comprises a vehicle which preferably comprises distilled water, alcohol, and the surfactant Brij 30 (made by ICI Americas Inc., located at Wilmington, Del.). Most preferably, the active ingredients in the vehicle are vitamin C (15%), vitamin E (1%), vitamin A (1%), and zinc sulfate (1%), plus olive extract (1%) obtained according to the invention herein.

The invention also includes a method of treating the skin, comprised of applying to the skin a product formulated in a composition containing the final extract, preferably formulated as above.

EXAMPLES

The features of the present invention will be more clearly understood by reference to the following examples, which are not to be construed as limiting the invention.

Example 1

Antioxidant Protection Factor

Yorkshire pigs were shaved 24 hours prior to exposure. 1.0 ml of antioxidant solution was applied daily to a 10×15 cm area of back skin for 4 days. A 1000 W xenon arc solar simulator was fitted with a dichroic mirror assembly with 1 mm WG 295 Schott selective UVB band-pass filter (295 nm). A fiber optic assembly delivered a 1 cm spot to the skin surface. An IL 1700 research radiometer with a UVA and UVB detector measured irradiance.

On day 3, pigs received solar-simulated radiation at irradiance (UVB) of 5 $mW/cm^2$ and fluences of 10–100 $mJ/cm^2$ at 10 $mJ/cm^2$ intervals to untreated skin to determine minimal erythema dose (MED). At this irradiance, there was about 40 $mW/cm^2$ of UVA MED was determined 24 hours later, and was defined as the lowest dose that induces perceptible erythema with distinct borders.

On day 4, each 10×15 cm area received solar-simulated radiation at fluences of 1×–10× MED at 1.0 MED intervals. After 24 hours, erythema was determined visually. Antioxidant protection factor was calculated for each formulation as the ratio of MED in antioxidant-treated versus untreated (control) sites. A formulation containing 20% L-ascorbic acid, 1% α-tocopherol, 1% retinol (vitamin A) and 1% olive leaf formulation was tested for antioxidant protection factor. The complete formulation gave sevenfold protection as compared to the control. L-ascorbic acid was essential. Removing retinol or olive extract reduced the protection to five-fold, and removing α-tocopherol reduced the protection to 4-fold. Results are shown in FIG. 1.

Example 2

Sunburn Cell Determination

Characteristic sunburn cells can be identified in the epidermis following UVR injury to skin and are usually enumerated 24 hours after exposure as a measure of photodamage. Eight-mm punch biopsy specimens from antioxidant-treated and control skin receiving solar-simulated radiation at 1×–10×-MED as described in Example 1 were placed in 10% buffered formalin for routine processing and paraffin-embedding. The tissue was stained with hematoxylin and eosin using standard techniques. Cells in the basal, spinous, and granular layers of the epidermis having pyknotic nucleus and hypereosinophilic, hyalinized cytoplasm were designated as sunburn cells. In each biopsy, the central section of the histologic ribbon was selected, and epidermal sunburn cells were enumerated by consensus opinion of two dermatopathologists viewing the slide simultaneously. The entire width of the specimen was viewed (approximately 16 high power fields) and the number of sunburn cells per linear mm of epidermis was calculated, not including hair follicles. It has been found that at levels above 35 sunburn cells/mm, that the damage is too great to distinguish sunburn cells precisely. Therefore, this level is used as the upper limit for calculations shown below. It is clear that each antioxidant ingredient in the formulation contributes and is essential for an optimal photoprotective effect. Results are shown in FIG. 2.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A product for application to skin comprising, by weight:
   a) at least about 0.5% of an extract of olive leaves obtained by steps comprising treatment of the olive leaves to inactivate enzymes therein, followed by extraction of the enzyme-inactivated olive leaves with a non-aqueous organic solvent to form an initial extract followed by purification and concentration thereof;
   b) 5–25% of L-ascorbic acid;
   c) 0.5–2% of a vitamin E component selected from the group consisting of tocopherols and tocotrienols; and
   d) 0.5–2% of vitamin A.

2. The product according to claim 1, wherein the extract of olive leaves is obtained by steps comprising:
   a) treating the olive leaves to inactivate enzymes in the olive leaves;
   b) continuously extracting the treated olive leaves with a non-aqueous solvent, purifying by filtration and concentrating to form a first paste;
   c) removing the non-aqueous solvent;
   d) suspending the first paste in water, boiling, filtering, and re-concentrating to form a second paste; and
   e) combining the second paste with alcohol and charcoal, boiling, filtering and re-concentrating to form a final extract, wherein said final extract contains about 6–10% oleuropein.

3. The product according to claim 2 comprising:
   a) 1% of the final extract of olive leaves;
   b) 15–20% L-ascorbic acid;
   c) 1–2% vitamin E component; and
   d) 1% vitamin A.

4. The product according to claim 1, further comprising a vehicle selected from the group consisting of distilled water, alcohol, and a surfactant.

5. The product according to claim 1 wherein the vitamin E component comprises α-tocopherol.

6. The product according to claim 1, wherein the extract of olive leaves comprises at least one antioxidant phenolic compound.

7. The product according to claim 6, wherein the antioxidant phenolic compound is selected from the group consisting of oleuropein and hydroxytyrosol.

8. The product according to claim 1, further comprising 1–5% zinc sulfate.

9. The product according to claim 1, wherein the pH of the product is about 2.0 to 4.5.

* * * * *